United States Patent
Kim et al.

(10) Patent No.: US 12,266,761 B2
(45) Date of Patent: Apr. 1, 2025

(54) ELECTROLYTE FOR LITHIUM SECONDARY BATTERY AND LITHIUM SECONDARY BATTERY INCLUDING THE SAME

(71) Applicant: LG Energy Solution, Ltd., Seoul (KR)

(72) Inventors: Hyun Seung Kim, Daejeon (KR); Yu Ha An, Daejeon (KR); Chul Haeng Lee, Daejeon (KR); Jeong Woo Oh, Daejeon (KR)

(73) Assignee: LG Energy Solution, Ltd., Seoul (KR)

( * ) Notice: Subject to any disclaimer, the term of this patent is extended or adjusted under 35 U.S.C. 154(b) by 687 days.

(21) Appl. No.: 17/431,890

(22) PCT Filed: Feb. 26, 2020

(86) PCT No.: PCT/KR2020/002732
§ 371 (c)(1),
(2) Date: Aug. 18, 2021

(87) PCT Pub. No.: WO2020/175907
PCT Pub. Date: Sep. 3, 2020

(65) Prior Publication Data
US 2022/0140391 A1    May 5, 2022

(30) Foreign Application Priority Data
Feb. 28, 2019    (KR) .................. 10-2019-0024104

(51) Int. Cl.
*H01M 10/05*    (2010.01)
*C07D 233/90*    (2006.01)
(Continued)

(52) U.S. Cl.
CPC ...... *H01M 10/0567* (2013.01); *C07D 233/90* (2013.01); *H01M 10/0525* (2013.01);
(Continued)

(58) Field of Classification Search
None
See application file for complete search history.

(56) References Cited

U.S. PATENT DOCUMENTS

| | | | |
|---|---|---|---|
| 6,413,679 B1 | 7/2002 | Kuboki et al. | |
| 2011/0045361 A1 | 2/2011 | Abe et al. | |

(Continued)

FOREIGN PATENT DOCUMENTS

| | | |
|---|---|---|
| CN | 103000942 A | 3/2013 |
| CN | 103975476 A | 8/2014 |

(Continued)

OTHER PUBLICATIONS

International Search Report for Application No. PCT/KR2020/002732, dated Jun. 9, 2020, 2 pages.

(Continued)

*Primary Examiner* — Jonathan G Leong
*Assistant Examiner* — Tony S Chuo
(74) *Attorney, Agent, or Firm* — Lerner David LLP

(57) ABSTRACT

The present invention relates to an electrolyte for a lithium secondary battery and a lithium secondary battery including the same. In some embodiments, the electrolyte includes a lithium salt, a first additive, a second additive, and an organic solvent, wherein the first additive includes a compound represented by Formula 1 and the second additive includes a compound represented by Formula 2.

10 Claims, 2 Drawing Sheets

(51) Int. Cl.
H01M 10/0525 (2010.01)
H01M 10/0567 (2010.01)
H01M 10/0568 (2010.01)
H01M 10/0569 (2010.01)

(52) U.S. Cl.
CPC ... H01M 10/0568 (2013.01); H01M 10/0569 (2013.01); H01M 2300/0028 (2013.01)

(56) References Cited

U.S. PATENT DOCUMENTS

| | | |
|---|---|---|
| 2011/0229769 A1 | 9/2011 | Ihara et al. |
| 2011/0311884 A1 | 12/2011 | Armand et al. |
| 2013/0230768 A1 | 9/2013 | Sakamoto et al. |
| 2014/0030609 A1 | 1/2014 | Abe et al. |
| 2015/0017551 A1 | 1/2015 | Schmidt |
| 2015/0315155 A1 | 11/2015 | Armand et al. |
| 2016/0197349 A1 | 7/2016 | Schmidt |
| 2016/0380309 A1 | 12/2016 | Schmidt et al. |
| 2018/0358655 A1 | 12/2018 | Kono et al. |
| 2019/0237805 A1 | 8/2019 | Lim et al. |
| 2019/0312309 A1 | 10/2019 | Schmidt et al. |
| 2020/0044287 A1 | 2/2020 | Kim et al. |
| 2020/0251777 A1 | 8/2020 | Lim et al. |
| 2021/0218060 A1 | 7/2021 | Paillet et al. |

FOREIGN PATENT DOCUMENTS

| | | | |
|---|---|---|---|
| CN | 108232296 | A | 6/2018 |
| EP | 3518334 | A1 | 7/2019 |
| JP | 2000106211 | A | 4/2000 |
| JP | 2011198508 | A | 10/2011 |
| JP | 2012500833 | A | 1/2012 |
| JP | 4997151 | B2 | 8/2012 |
| JP | 5610052 | B2 | 10/2014 |
| JP | 5862562 | B2 | 2/2016 |
| JP | 2020528640 | A | 9/2020 |
| KR | 20070083086 | A | 8/2007 |
| KR | 20140034187 | A | 3/2014 |
| KR | 20160052658 | A | 5/2016 |
| KR | 20160133521 | A | 11/2016 |
| KR | 20170132239 | A | 12/2017 |
| KR | 2018-0106970 | A | 10/2018 |
| KR | 20190008100 | A | 1/2019 |
| WO | 2016158986 | A1 | 10/2016 |
| WO | 2018100297 | A1 | 6/2018 |
| WO | 2018163127 | A1 | 9/2018 |
| WO | WO 2018/169370 A1 * | | 9/2018 ........ H01M 10/0567 |
| WO | 2019013501 | A1 | 1/2019 |

OTHER PUBLICATIONS

L. Niedzicki et al: "New type of imidazole based salts designed specifically for lithium ion batteries", Electrochimica Acta, vol. 55, No. 4, May 13, 2009 (May 13, 2009), pp. 1450-1454, XP026867410.
Extended European Search Report for Application No. 20762755.5 dated Feb. 23, 2022. 10 pgs.

* cited by examiner

ELECTROLYTE FOR LITHIUM SECONDARY BATTERY AND LITHIUM SECONDARY BATTERY INCLUDING THE SAME

CROSS-REFERENCE TO RELATED APPLICATIONS

The present application is a national phase entry under 35 U.S.C. § 371 of International Application No. PCT/KR2020/002732, filed on Feb. 26, 2020, which claims priority from Korean Patent Application No. 2019-0024104, filed on Feb. 28, 2019, the disclosure of which is incorporated by reference herein.

TECHNICAL FIELD

The present invention relates to an electrolyte for a lithium secondary battery having excellent high-temperature characteristics and a lithium secondary battery including the same.

BACKGROUND ART

There is a need to develop technology for efficiently storing and utilizing electrical energy as personal IT devices and computer networks are developed with the development of information society and the accompanying dependency of society as a whole on the electrical energy is increased.

A technology based on secondary batteries is the most suitable technology for various applications, wherein, since a secondary battery may be miniaturized, it is applicable to a personal IT device, and it is also applicable to a large device such as a power storage device.

Among these secondary battery technologies, lithium ion batteries, which are battery systems having the theoretically highest energy density, are in the spotlight.

The lithium ion battery is largely composed of a positive electrode formed of a transition metal oxide containing lithium, a negative electrode capable of storing lithium, an electrolyte that becomes a medium for transferring lithium ions, and a separator. Among them, a significant amount of research on the electrolyte has been conducted while the electrolyte is known as a component that greatly affects stability and safety of the battery.

The electrolyte causes a reduction decomposition reaction during an activation process of the battery, and a reduced and decomposed product forms a solid electrolyte interphase (SEI) that transmits lithium ions on an interface of the negative electrode, but suppresses additional decomposition of the electrolyte.

Since the SEI does not have electronic conductivity but has ionic conductivity, the SEI plays a role in assisting the movement of the lithium ions.

In a case in which the SEI does not have sufficient passivation ability to such an extent that it may suppress the additional decomposition of the electrolyte, since the electrolyte is additionally decomposed during storage, charged graphite is self-discharged, and, as a result, a phenomenon occurs in which a potential of the entire secondary battery is reduced. For example, under high-temperature conditions, since a by-product, which is generated by a decomposition reaction of a lithium salt included in the electrolyte, is activated and then rather decomposes the SEI formed on surfaces of the positive electrode and the negative electrode, passivation ability of the SEI is reduced, and, as a result, the electrolyte is additionally decomposed to cause self-discharge.

Thus, in order to maintain the passivation ability of the SEI under high-temperature conditions, there is an urgent need for research into an electrolyte which includes a component capable of suppressing the generation of a decomposition product of the salt.

PRIOR ART DOCUMENT

Korean Patent Application Laid-open Publication No. 10-2017-0132239

DISCLOSURE OF THE INVENTION

Technical Problem

An aspect of the present invention provides an electrolyte for a lithium secondary battery which may remove a by-product generated due to a decomposition reaction of a lithium salt at high temperature.

Another aspect of the present invention provides a lithium secondary battery in which high-temperature life characteristics and high-temperature storage characteristics are improved by including the electrolyte for a lithium secondary battery.

Technical Solution

According to an aspect of the present invention, there is provided an electrolyte for a lithium secondary battery which includes: a lithium salt, a first additive, a second additive, and an organic solvent, wherein the first additive includes a compound represented by Formula 1 below, and the second additive includes a compound represented by Formula 2 below.

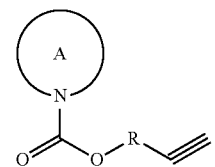

[Formula 1]

In Formula 1, R is a substituted or unsubstituted alkylene group having 1 to 5 carbon atoms, and A is a substituted or unsubstituted hetero ring connected by the nitrogen (N) to the remainder of Formula 1, the substituted or unsubstituted hetero ring having 3 to 8 carbon atoms which contains at least one nitrogen atom and at least one double bond

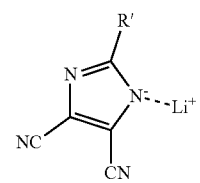

[Formula 2]

In Formula 2, R' is at least one functional group selected from the group consisting of F, $CF_3$, $CHF_2$, $CH_2F$, $C_2HF_4$, $C_2H_2F_3$, $C_2H_3F_2$, $C_2F_5$, $C_3F_7$, $C_3H_2F_5$, $C_3H_4F_3$, $C_4F_9$, $C_4H_2F_7$, $C_4H_4F_5$, $C_5F_{11}$, $C_3F_5OCF_3$, $C_2F_4OCF_3$, $C_2H_2F_2OCF_3$, and $CF_2OCF_3$.

According to another aspect of the present invention, there is provided a lithium secondary battery including a positive electrode; a negative electrode; and the electrolyte for a lithium secondary battery of the present invention.

Advantageous Effects

A compound represented by Formula 1 and a compound represented by Formula 2, which are included in an electrolyte for a lithium secondary battery of the present invention, are compounds containing a nitrogen (N) atom in their structures, wherein, since the N atom acts as a Lewis base to scavenge a Lewis acid generated as an electrolyte decomposition product under high-temperature conditions, the compounds may suppress additional decomposition of an organic solvent in the electrolyte. Thus, since an increase in resistance in the battery may be minimized and a degradation of battery life characteristics may be minimized by preventing a damage of a solid electrolyte interphase (SEI) formed on an electrode interface by a reaction by-product in advance, a lithium secondary battery having improved high-temperature life characteristics and high-temperature storage characteristics may be achieved.

BRIEF DESCRIPTION OF THE DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

MODE FOR CARRYING OUT THE INVENTION

Figure 1:
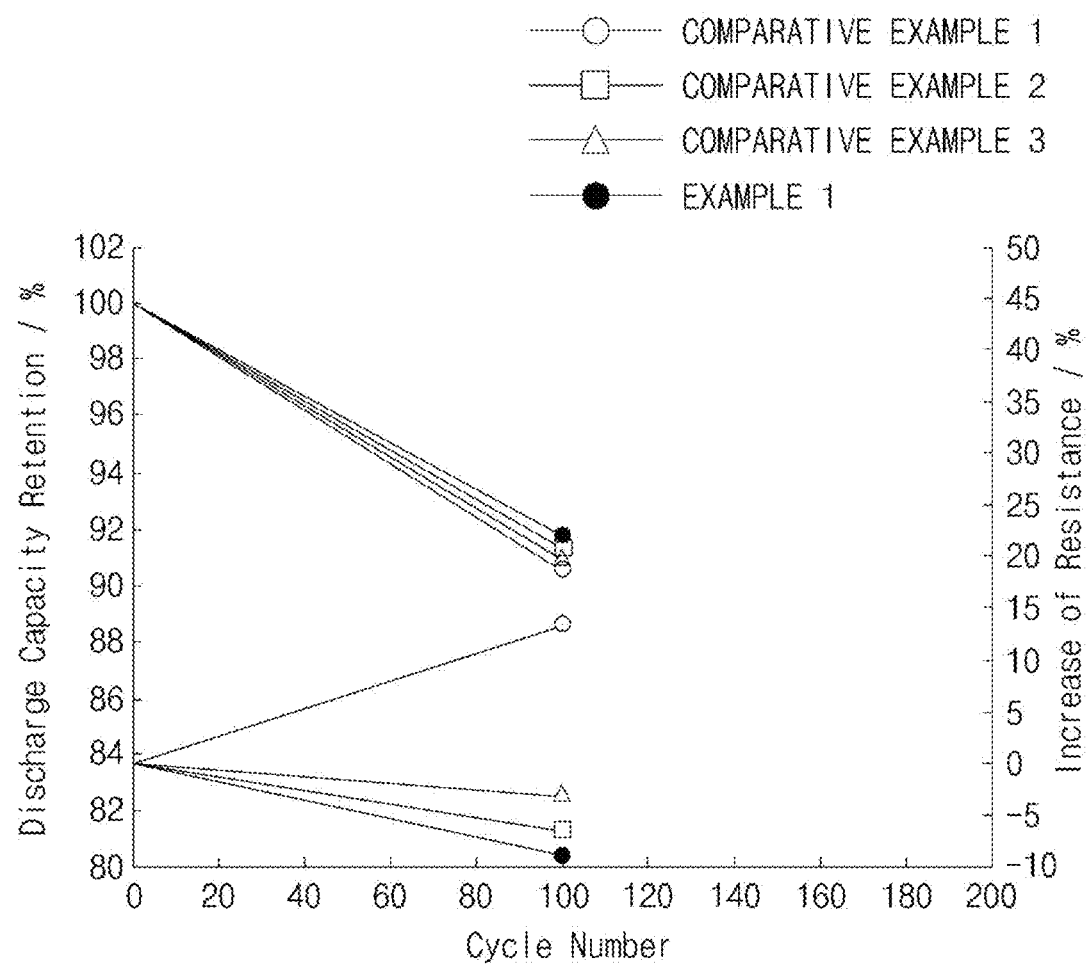
FIG. 1 is a graph illustrating capacity retentions and resistance increase rates of lithium secondary batteries measured according to Experimental Example 1.

Hereinafter, the present invention will be described in more detail.

It will be understood that words or terms used in the specification and claims shall not be interpreted as the meaning defined in commonly used dictionaries, and it will be further understood that the words or terms should be interpreted as having a meaning that is consistent with their meaning in the context of the relevant art and the technical idea of the invention, based on the principle that an inventor may properly define the meaning of the words or terms to best explain the invention.

The terminology used herein is for the purpose of describing particular example embodiments only and is not intended to be limiting of the present invention. In the specification, the terms of a singular form may comprise plural forms unless referred to the contrary.

It will be further understood that the terms "include," "comprise," or "have" when used in this specification, specify the presence of stated features, numbers, steps, elements, or combinations thereof, but do not preclude the presence or addition of one or more other features, numbers, steps, elements, or combinations thereof.

<Electrolyte for Lithium Secondary Battery>

An electrolyte for a lithium secondary battery according to the present invention includes: a lithium salt, a first additive, a second additive, and an organic solvent, wherein the first additive includes a compound represented by Formula 1 below, and the second additive includes a compound represented by Formula 2 below.

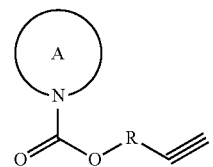

[Formula 1]

In Formula 1, R is a substituted or unsubstituted alkylene group having 1 to 5 carbon atoms, and A is a substituted or unsubstituted hetero ring connected by the nitrogen (N) to the remainder of Formula 1, the substituted or unsubstituted hetero ring having 3 to 8 carbon atoms which contains at least one nitrogen atom and at least one double bond.

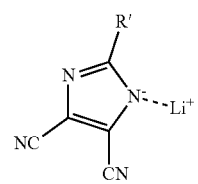

[Formula 2]

In Formula 2, R' is at least one functional group selected from the group consisting of F, $CF_3$, $CHF_2$, $CH_2F$, $C_2HF_4$, $C_2H_2F_3$, $C_2H_3F_2$, $C_2F_5$, $C_3F_7$, $C_3H_2F_5$, $C_3H_4F_3$, $C_4F_9$, $C_4H_2F_7$, $C_4H_4F_5$, $C_5F_{11}$, $C_3F_5OCF_3$, $C_2F_4OCF_3$, $C_2H_2F_2OCF_3$, and $CF_2OCF_3$.

(1) Lithium Salt

First, a lithium salt will be described.

The lithium salt is used as a medium for transferring ions in a lithium secondary battery. Typically, the lithium salt may include at least one compound selected from the group consisting of $LiPF_6$, $LiBF_4$, $LiSbF_6$, $LiAsF_6$, $LiClO_4$, $LiN(C_2F_5SO_2)_2$, $LiN(CF_3SO_2)_2$, $CF_3SO_3Li$, $LiC(CF_3SO_2)_3$, $LiC_4BO_8$, LiTFSI, LiFSI, and $LiClO_4$, and may preferably include $LiPF_6$ and/or $LiBF_4$.

Among the lithium salts, $LiPF_6$ and/or $LiBF_4$ are particularly widely used because they have relatively higher ionic conductivity than other lithium salts. However, in a case in which an organic solvent included in an electrolyte is decomposed at high temperature, if a decomposition product of the organic solvent and $PF_6^-$, as an anion of the lithium salt, which is generated by dissolution of the lithium salt in the organic solvent, react with each other, a Lewis acid by-product, such as $PF_5$, may be generated. With respect to the Lewis acid by-product, it promotes a spontaneous decomposition reaction of the organic solvent and causes a side reaction that collapses a solid electrolyte interphase (SEI) formed on an electrode interface. In a case in which the side reaction is not suppressed, resistance in the battery may be rapidly increased, and capacity characteristics of the battery may be degraded.

Specifically, in a case in which $LiPF_6$ is used as the lithium salt, $PF_6^-$, as an anion, may lose electrons on a negative electrode side and $PF_5$ may be formed. In this case, a chemical reaction, such as the following Reaction Formula 1, may proceed in a chain-wise manner.

$$LiPF_6 \leftrightarrows LiF + PF_5$$

$$PF_5 + H_2O \rightarrow POF_3 + 2HF$$

$$POF_3 + H_2O \rightarrow POF_2(OH) + HF$$

$$POF_3 + 2xLi^+ + 2xe^- \rightarrow Li_xPF_{3-x}O + xLiF \qquad \text{[Reaction Formula 1]}$$

In a case in which the chain reaction is in progress, since other by-products, including HF generated, may cause the decomposition of the organic solvent or the side reaction with the SEI, performance of the battery may be continuously degraded.

(2) First Additive

In order to remove the by-products generated due to the chain reaction as in the Reaction Formula 1, an additive including a compound represented by the following Formula 1 is used in the electrolyte for a lithium secondary battery of the present invention.

[Formula 1]

In Formula 1, R is a substituted or unsubstituted alkylene group having 1 to 5 carbon atoms, and A is a substituted or unsubstituted hetero ring connected by the nitrogen (N) to the remainder of Formula 1, the substituted or unsubstituted hetero ring having 3 to 8 carbon atoms which contains at least one nitrogen atom and at least one double bond.

For example, the compound represented by Formula 1 may include at least one compound selected from the group consisting of compounds represented by Formulae 1A to 10 below.

[Formula 1A]

[Formula 1B]

[Formula 1C]

In Formulae 1A to 10, R is a substituted or unsubstituted alkylene group having 1 to 5 carbon atoms, and $R_1$ to $R_3$ are each independently selected from the group consisting of hydrogen, an alkyl group having 1 to 5 carbon atoms, and an alkyl group having 1 to 5 carbon atoms in which at least one hydrogen element is substituted with a halogen element.

Specifically, the compound represented by Formula 1 may be selected from compounds represented by Formulae 1A-1 to 1A-5 below.

[Formula 1A-1]

[Formula 1A-2]

[Formula 1A-3]

[Formula 1A-4]

[Formula 1A-5]

$PF_5$, one of by-products generated when the lithium salt dissolved in the organic solvent is decomposed under high-temperature conditions, corresponds to a Lewis acid compound. The Lewis acid compound, such as $PF_5$, may react with the organic solvent or components constituting the SEI on the electrode interface to cause a decomposition reaction. Thus, it is necessary to scavenge the Lewis acid compound, as a high-temperature decomposition product of the lithium salt, in order to address problems, such as an increase in resistance in the battery and a degradation of battery life characteristics, due to the generation of the decomposition reaction product by suppressing the decomposition reaction of the SEI under high-temperature conditions.

A Lewis acid compound is a chemical species that accepts an electron pair, and a Lewis base is a chemical species capable of donating an electron pair, wherein a compound having strong electron-donating characteristics may be used as the Lewis base.

Thus, in the present invention, a compound corresponding to the Lewis base, which may react with the Lewis acid, was used as the additive included in the electrolyte. Since ring A in the compound represented by Formula 1 contains at least one nitrogen element having an unshared electron pair and a triple bond at its end, it provides electrons to the Lewis acid compound such as $PF_5$, and thus, it performs a Lewis acid-base reaction with $PF_5$ instead of the components constituting the SEI formed on an electrode. Therefore, a damage of the SEI formed on the electrode may be prevented in advance by scavenging the $PF_5$.

Since the triple bond located at the end of the compound represented by Formula 1 may modify the SEI components, it may more stably form the SEI, and thus, it may also improve high-temperature stability of the SEI itself.

The first additive may be included in an amount of 0.02 part by weight to 1.0 part by weight, preferably 0.3 part by weight to 1.0 part by weight, and more preferably 0.1 part by weight to 0.7 part by weight based on 100 parts by weight of the electrolyte for a lithium secondary battery. In a case in which the first additive is included in an amount within the above range, the first additive may stably form a SEI while sufficiently scavenging the Lewis acid compound.

(3) Second Additive

Also, the electrolyte for a lithium secondary battery of the present invention includes a compound represented by the following Formula 2 as a second additive.

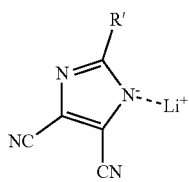

[Formula 2]

In Formula 2, R' is at least one functional group selected from the group consisting of F, $CF_3$, $CHF_2$, $CH_2F$, $C_2HF_4$, $C_2H_2F_3$, $C_2H_3F_2$, $C_2F_5$, $C_3F_7$, $C_3H_2F_5$, $C_3H_4F_3$, $C_4F_9$, $C_4H_2F_7$, $C_4H_4F_5$, $C_5F_{11}$, $C_3F_5OCF_3$, $C_2F_4OCF_3$, $C_2H_2F_2OCF_3$, and $CF_2OCF_3$.

The compound represented by Formula 2 forms a SEI on a surface of a negative electrode while being decomposed, wherein, since the SEI including a decomposition product of the compound represented by Formula 2 may be more robustly formed in comparison to a case where the compound represented by Formula 1 is only used, high-temperature durability of the battery may be improved.

Specifically, lithium 4,5-dicyano-2-(trifluoromethyl)imidazole (LiTDI) may be used as the compound represented by Formula 2.

The second additive may be included in an amount of 0.02 part by weight to 1.0 part by weight, preferably 0.3 part by weight to 1.0 part by weight, and more preferably 0.3 part by weight to 0.7 part by weight based on 100 parts by weight of the electrolyte for a lithium secondary battery. In a case in which the lithium imidazole salt represented by Formula 2 is included in an amount within the above range, it may improve the high-temperature durability by forming a stable SEI on the negative electrode while minimizing an increase in initial resistance of the battery.

(4) Other Additives

The electrolyte for a lithium secondary battery according to the present invention may further include other additives which may form a stable film on the surfaces of the negative electrode and positive electrode while not significantly increasing the initial resistance, or which may act as a complementary agent for suppressing the decomposition of the solvent in the electrolyte and improving mobility of lithium ions.

For example, the other additives may include at least one compound selected from the group consisting of a vinyl silane-based compound, a phosphate-based or phosphite-based compound, a sulfite-based compound, a sulfone-based compound, a sulfate-based compound, a sultone-based compound, a halogen-substituted carbonate-based compound, a nitrile-based compound, a borate-based compound, and a lithium salt-based compound.

The vinyl silane-based compound may improve durability of the battery by forming a stable SEI through electrochemical reduction at the surface of the negative electrode. Specifically, tetravinylsilane may be included as the vinyl silane-based compound.

The phosphate-based or phosphite-based compound is a component for assisting the formation of the SEI by being electrochemically decomposed on the surfaces of the positive electrode and the negative electrode, wherein it may improve life characteristics of the secondary battery. Specifically, the phosphate-based or phosphite-based compound may include at least one compound selected from the group consisting of lithium difluoro(bisoxalato)phosphate, lithium difluorophosphate, tris(trimethylsilyl) phosphate, tris(trimethylsilyl) phosphite, tris(2,2,2-trifluoroethyl) phosphate, and tris(trifluoroethyl) phosphite.

The sulfite-based compound may include at least one compound selected from the group consisting of ethylene sulfite, methylethylene sulfite, ethylethylene sulfite, 4,5-dimethylethylene sulfite, 4,5-diethylethylene sulfite, propylene sulfite, 4,5-dimethylpropylene sulfite, 4,5-diethylpropylene sulfite, 4,6-dimethylpropylene sulfite, 4,6-diethylpropylene sulfite, and 1,3-butylene glycol sulfite.

The sulfone-based compound may include at least one compound selected from the group consisting of divinyl sulfone, dimethyl sulfone, diethyl sulfone, methylethyl sulfone, and methylvinyl sulfone.

The sulfate-based compound may include at least one compound selected from the group consisting of ethylene sulfate (Esa), trimethylene sulfate (TMS), and methyl trimethylene sulfate (MTMS).

The sultone-based compound may include at least one compound selected from the group consisting of 1,3-propane sultone (PS), 1,4-butane sultone, ethane sultone, 1,3-propene sultone (PRS), 1,4-butene sultone, and 1-methyl-1,3-propene sultone.

As the halogen-substituted carbonate-based compound, fluoroethylene carbonate (FEC) may be included.

Also, the nitrile-based compound may include at least one compound selected from the group consisting of succinonitrile (SN), adiponitrile (Adn), acetonitrile, propionitrile, butyronitrile, valeronitrile, caprylonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile, and 4-fluorophenylacetonitrile.

The borate-based compound may include lithium oxalyldifluoroborate (LiODFB) or lithium bis(oxalato)borate ($LiB(C_2O_4)_2$: LiBOB).

The lithium salt-based compound is a compound different from the lithium salt included in the electrolyte, wherein the lithium salt-based compound may include at least one compound selected from the group consisting of $LiPO_2F_2$ and $LiBF_4$.

The other additives may be included in an amount of 20 parts by weight or less, for example, 10 parts by weight or less based on 100 parts by weight of the electrolyte for a lithium secondary battery. If the amount of the additives is greater than the above range, a side reaction may excessively occur in the electrolyte during charge and discharge of the lithium secondary battery, and, since the additives are not sufficiently decomposed at high temperatures, the additives may be present in the electrolyte in the form of an unreacted material or precipitates, and, accordingly, life or resistance characteristics of the secondary battery may be degraded.

(5) Organic Solvent

Next, the organic solvent will be described.

In the present invention, the organic solvent is a solvent commonly used in a lithium secondary battery, wherein, for example, an ether compound, an ester compound (acetates and propionates), an amide compound, a linear carbonate compound, a cyclic carbonate compound, or a nitrile compound may be used alone or in mixture of two or more thereof.

Among them, the cyclic carbonate compound, the linear carbonate compound, or a carbonate compound, as a mixture thereof, may be typically used as the organic solvent.

Specific examples of the cyclic carbonate compound may be a single compound selected from the group consisting of ethylene carbonate (EC), propylene carbonate (PC), 1,2-butylene carbonate, 2,3-butylene carbonate, 1,2-pentylene carbonate, 2,3-pentylene carbonate, vinylene carbonate, and halides thereof, or a mixture of two or more thereof. Also, as specific examples of the linear carbonate compound, a compound selected from the group consisting of dimethyl carbonate (DMC), diethyl carbonate (DEC), dipropyl carbonate (DPC), ethylmethyl carbonate (EMC), methylpropyl carbonate (MPC), and ethylpropyl carbonate (EPC), or a mixture of two or more thereof may be typically used, but the present invention is not limited thereto.

In particular, since propylene carbonate and ethylene carbonate, as the cyclic carbonate compounds, are highly viscous organic solvents and have high dielectric constants, the propylene carbonate and ethylene carbonate may well dissociate the lithium salt in the electrolyte, and, thus, the propylene carbonate and ethylene carbonate may be preferably used. Since an electrolyte having high electrical conductivity may be prepared when the above cyclic carbonate compound is mixed with the low viscosity, low dielectric constant linear carbonate compound, such as ethylmethyl carbonate, diethyl carbonate, or dimethyl carbonate, in an appropriate ratio, the propylene carbonate and ethylene carbonate may be more preferably used.

Furthermore, as the ester compound among the organic solvents, a single compound selected from the group consisting of methyl acetate, ethyl acetate, propyl acetate, methyl propionate, ethyl propionate, γ-butyrolactone, γ-valerolactone, γ-caprolactone, σ-valerolactone, and ε-caprolactone, or a mixture of two or more thereof may be used, but the present invention is not limited thereto.

<Lithium Secondary Battery>

Next, a lithium secondary battery according to the present invention will be described.

The lithium secondary battery according to an embodiment of the present invention includes a positive electrode, a negative electrode, a separator which may be selectively disposed between the positive electrode and the negative electrode, and the electrolyte for a lithium secondary battery. In this case, since the electrolyte for a lithium secondary battery is the same as described above, a detailed description thereof will be omitted.

(1) Positive Electrode

The positive electrode may be prepared by coating a positive electrode collector with a positive electrode active material slurry including a positive electrode active material, a binder for an electrode, a conductive agent for an electrode, and a solvent.

The positive electrode collector is not particularly limited so long as it has conductivity without causing adverse chemical changes in the battery, and, for example, stainless steel, aluminum, nickel, titanium, fired carbon, or aluminum or stainless steel that is surface-treated with one of carbon, nickel, titanium, silver, or the like may be used. In this case, the positive electrode collector may have fine surface roughness to improve bonding strength with the positive electrode active material, and the positive electrode collector may be used in various shapes such as a film, a sheet, a foil, a net, a porous body, a foam body, a non-woven fabric body, and the like.

The positive electrode active material is a compound capable of reversibly intercalating and deintercalating lithium, wherein the positive electrode active material may specifically include a lithium composite metal oxide including lithium and at least one metal such as cobalt, manganese, nickel, or aluminum. Specifically, the lithium composite metal oxide may include lithium-manganese-based oxide (e.g., $LiMnO_2$, $LiMn_2O_4$, etc.), lithium-cobalt-based oxide (e.g., $LiCoO_2$, etc.), lithium-nickel-based oxide (e.g., $LiNiO_2$, etc.), lithium-nickel-manganese-based oxide (e.g., $LiNi_{1-Y1}Mn_{Y1}O_2$ (where 0<Y1<1), $LiMn_{2-Z1}Ni_{z1}O_4$ (where 0<Z1<2), etc.), lithium-nickel-cobalt-based oxide (e.g., $LiNi_{1-Y2}Co_{Y2}O_2$ (where 0<Y2<1), lithium-manganese-cobalt-based oxide (e.g., $LiCo_{1-Y3}Mn_{Y3}O_2$ (where 0<Y3<1), $LiMn_{2-Z2}Co_{Z2}O_4$ (where 0<Z2<2), etc.), lithium-nickel-manganese-cobalt-based oxide (e.g., $Li(Ni_{p1}Co_{q1}Mn_{r1})O_2$ (where 0<p1<1, 0<q1<1, 0<r1<1, and p1+q1+r1=1) or $Li(Ni_{p2}Co_{q2}Mn_{r2})O_4$ (where 0<p2<2, 0<q2<2, 0<r2<2, and p2+q2+r2=2), etc.), or lithium-nickel-cobalt-transition metal (M) oxide (e.g., $Li(Ni_{p3}Co_{q3}Mn_{r3}Mn_{S1})O_2$ (where M is selected from the group consisting of aluminum (Al), iron (Fe), vanadium (V), chromium (Cr), titanium (Ti), tantalum (Ta), magnesium (Mg), and molybdenum (Mo), and p3, q3, r3, and s1 are atomic fractions of each independent elements, wherein 0<p3<1, 0<q3<1, 0<r3<1, 0<S1<1, and p3+q3+r3+S1=1), etc.), and any one thereof or a compound of two or more thereof may be included.

Among these materials, in terms of the improvement of capacity characteristics and stability of the battery, the lithium composite metal oxide may include $LiCoO_2$, $LiMnO_2$, $LiNiO_2$, lithium nickel manganese cobalt oxide (e.g., $Li(Ni_{0.6}Mn_{0.2}Co_{0.2})O_2$, $Li(Ni_{0.5}Mn_{0.3}Co_{0.2})O_2$, or $Li(Ni_{0.8}Mn_{0.1}Co_{0.1})O_2$), or lithium nickel cobalt aluminum oxide (e.g., $LiNi_{0.8}Co_{0.15}Al_{0.05}O_2$, etc.), and, in consideration of a significant improvement due to the control of type and content ratio of elements constituting the lithium composite metal oxide, the lithium composite metal oxide may include $Li(Ni_{0.6}Mn_{0.2}Co_{0.2})O_2$, $Li(Ni_{0.5}Mn_{0.3}Co_{0.2})O_2$, $Li(Ni_{0.7}Mn_{0.15}Co_{0.15})O_2$, or $Li(Ni_{0.8}Mn_{0.1}Co_{0.1})O_2$, and any one thereof or a mixture of two or more thereof may be used.

The binder for an electrode is a component that assists in the binding between the positive electrode active material and the electrode conductive agent and in the binding with the current collector. Specifically, the binder may include polyvinylidene fluoride, polyvinyl alcohol, carboxymethylcellulose (CMC), starch, hydroxypropylcellulose, regenerated cellulose, polyvinylpyrrolidone, polytetrafluoroethylene, polyethylene (PE), polypropylene, an ethylene-propylene-diene terpolymer, a sulfonated ethylenepropylene-diene terpolymer, a styrene-butadiene rubber, styrene-butadiene rubber-carboxymethylcellulose (SBR-CMC), a fluoro rubber, various copolymers thereof, and the like.

The conductive agent for an electrode is a component for further improving the conductivity of the positive electrode active material. Any conductive agent for an electrode may be used without particular limitation so long as it has conductivity without causing adverse chemical changes in the battery, and, for example, a conductive material, such as: graphite; a carbon-based material such as carbon black, acetylene black, Ketjen black, channel black, furnace black, lamp black, and thermal black; conductive fibers such as carbon fibers or metal fibers; metal powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used. Specific examples of a commercial conductive agent may include acetylene black-based products (Chevron Chemical Company, Denka black (Denka Singapore Private Limited), or Gulf Oil Company), Ketjen black, ethylene carbonate (EC)-based products (Armak Company), Vulcan XC-72 (Cabot Company), and Super P (Timcal Graphite & Carbon).

The solvent may include an organic solvent, such as N-methyl-2-pyrrolidone (NMP), and may be used in an amount such that desirable viscosity is obtained when the positive electrode active material as well as selectively the binder for an electrode and the conductive agent for an electrode is included.

(2) Negative Electrode

Also, the negative electrode, for example, may be prepared by coating a negative electrode collector with a negative electrode active material slurry including a negative electrode active material, a binder for an electrode, a conductive agent for an electrode, and a solvent. A metal current collector itself may be used as the negative electrode.

The negative electrode collector is not particularly limited so long as it has high conductivity without causing adverse chemical changes in the battery, and, for example, copper, stainless steel, aluminum, nickel, titanium, fired carbon, copper or stainless steel that is surface-treated with one of carbon, nickel, titanium, silver, or the like, an aluminum-cadmium alloy, or the like may be used. Also, similar to the positive electrode collector, the negative electrode collector may have fine surface roughness to improve bonding strength with the negative electrode active material, and the negative electrode collector may be used in various shapes such as a film, a sheet, a foil, a net, a porous body, a foam body, a non-woven fabric body, and the like.

The negative electrode active material may include at least one negative electrode active material selected from the group consisting of natural graphite, artificial graphite, a carbonaceous material; lithium-containing titanium composite oxide (LTO); metals (Me) such as silicon (Si), tin (Sn), lithium (Li), zinc (Zn), Mg, cadmium (Cd), cerium (Ce), nickel (Ni), or Fe; alloys composed of the metals (Me); oxides of the metals (Me); and composites of the metals (Me) and carbon.

Since the binder for an electrode, the conductive agent for an electrode, and the solvent are the same as described above, detailed descriptions thereof will be omitted.

(3) Separator

A typical porous polymer film used as a typical separator, for example, a porous polymer film prepared from a polyolefin-based polymer, such as an ethylene homopolymer, a propylene homopolymer, an ethylene-butene copolymer, an ethylene-hexene copolymer, and an ethylene-methacrylate copolymer, may be used alone or in a lamination therewith as the separator, and a polyolefin-based porous polymer film coated with inorganic particles (e.g. $Al_2O_3$) or a typical porous nonwoven fabric, for example, a nonwoven fabric formed of high melting point glass fibers or polyethylene terephthalate fibers may be used, but the present invention is not limited thereto.

Hereinafter, the present invention will be described in detail, according to specific examples. However, the following examples are merely presented to exemplify the present invention, and the scope of the present invention is not limited thereto. It will be apparent to those skilled in the art that various modifications and alterations are possible within the scope and technical spirit of the present invention. Such modifications and alterations fall within the scope of claims included herein.

EXAMPLES

1. Example 1

(1) Preparation of Electrolyte for Lithium Secondary Battery

A non-aqueous solvent was prepared by dissolving $LiPF_6$ and LiFSI in an organic solvent, in which ethylene carbonate (EC) and ethyl methyl carbonate (EMC) were mixed in a volume ratio of 3:7, such that concentrations of the $LiPF_6$ and the LiFSI were 0.7 M and 0.3 M, respectively. 0.5 g of the compound represented by Formula 1A-1 as a first additive, 0.5 g of lithium 4,5-dicyano-2-(trifluoromethyl) imidazole (manufactured by Aldrich, CAS: 761441-54-7) as a second additive, and 0.2 g of tetravinylsilane, 1.0 g of lithium difluorophosphate, 1.0 g of ethylene sulfonate, 0.5 g of 1,3-propane sultone, 0.2 g of $LiBF_4$, and 6.0 g of fluorobenzene, as other additives, were added to 90.1 g of the non-aqueous solvent to prepare an electrolyte for a lithium secondary battery.

(2) Lithium Secondary Battery Preparation

A positive electrode active material ($LiNi_{0.8}Co_{0.1}Mn_{0.1}O_2$; NCM811), carbon black as a conductive agent, and polyvinylidene fluoride (PVDF), as a binder, were mixed in a weight ratio of 97.5:1:1.5 and then added to N-methyl-2-pyrrolidone (NMP), as a solvent, to prepare a positive electrode active material slurry (solid content: 50 wt %). A 12 μm thick aluminum (Al) thin film, as a positive electrode collector, was coated with the positive electrode active material slurry, dried, and then roll-pressed to prepare a positive electrode.

A negative electrode active material (SiO:graphite=5:95 weight ratio), carbon black as a conductive agent, and styrene-butadiene rubber-carboxymethylcellulose (SBR-CMC), as a binder, were mixed in a weight ratio of 95:1.5:3.5 and then added to water, as a solvent, to prepare a negative electrode active material slurry (solid content: 60 wt %). A 6 μm thick copper (Cu) thin film, as a negative electrode collector, was coated with the negative electrode active material slurry, dried, and then roll-pressed to prepare a negative electrode.

An electrode assembly was prepared by sequentially stacking the positive electrode, a polyolefin-based porous separator coated with inorganic particles ($Al_2O_3$), and the negative electrode. Thereafter, the electrode assembly was accommodated in a pouch-type battery case, and the electrolyte for a lithium secondary battery was injected thereinto to prepare a pouch-type lithium secondary battery.

COMPARATIVE EXAMPLES

1. Comparative Example 1

An electrolyte for a lithium secondary battery and a lithium secondary battery were prepared in the same manner as in Example 1 except that, both the first additive and the second additive were not added, and 0.2 g of tetravinylsilane, 1.0 g of lithium difluorophosphate, 1.0 g of ethylene sulfonate, 0.5 g of 1,3-propane sultone, 0.2 g of $LiBF_4$, and 6.0 g of fluorobenzene were added to 91.1 g of the non-aqueous solvent.

2. Comparative Example 2

An electrolyte for a lithium secondary battery and a lithium secondary battery were prepared in the same manner as in Example 1 except that the first additive was not added, and 1.0 g of lithium 4,5-dicyano-2-(trifluoromethyl)imidazole as the second additive, and 0.2 g of tetravinylsilane, 1.0 g of lithium difluorophosphate, 1.0 g of ethylene sulfonate, 0.5 g of 1,3-propane sultone, 0.2 g of $LiBF_4$, and 6.0 g of fluorobenzene, as other additives, were added 90.1 g of the non-aqueous solvent.

3. Comparative Example 3

An electrolyte for a lithium secondary battery and a lithium secondary battery were prepared in the same manner as in Example 1 except that, the second additive was not added, and 1.0 g of the compound represented by Formula 1A-1 as the first additive, and 0.2 g of tetravinylsilane, 1.0 g of lithium difluorophosphate, 1.0 g of ethylene sulfonate, 0.5 g of 1,3-propane sultone, 0.2 g of $LiBF_4$, and 6.0 g of fluorobenzene, as other additives, were added 90.1 g of the non-aqueous solvent.

EXPERIMENTAL EXAMPLES

1. Experimental Example 1: High-Temperature (45° C.) Life Characteristics Evaluation After each of the lithium secondary batteries prepared in Example 1 and Comparative Examples 1 to 3 was activated at a CC of 0.1 C, degassing was performed. Thereafter, each lithium secondary battery was charged at a CC of 0.33 C to 4.20 V under a constant current-constant voltage (CC-CV) condition at 25° C., then subjected to 0.05 C current cut-off, and discharged at a CC of 0.33 C to 2.5 V. The above charging and discharging were defined as one cycle, and 3 cycles were performed.

Next, each lithium secondary battery was charged at a CC of 0.33 C to 4.20 V under a constant current-constant voltage (CC-CV) condition at 45° C., then subjected to 0.05 C current cut-off, and discharged at 0.33 C under a CC condition to 2.5 V. The above charging and discharging were defined as one cycle, and 100 cycles were repeated at a high temperature (45° C.). In this case, discharge capacity after one cycle was defined as initial discharge capacity. After the initial discharge capacity and discharge capacity after 100 cycles were respectively measured using PNE-0506 charge/discharge equipment (manufacturer: PNE SOLUTION Co., Ltd., 5 V, 6 A), these discharge capacities were substituted into the following [Equation 1] to calculate discharge capacity retention (%), and the results thereof are presented in FIG. 1.

Discharge capacity retention (%)=(discharge capacity after 100 cycles/initial discharge capacity)×100 (%) [Equation 1]

Each of the batteries in a state of being subjected to one cycle at 45° C. (initial state) and in a state of being subjected to 100 cycles at 45° C. was charged to a state of charge (SOC) of 50% at 25° C. Thereafter, direct current internal resistance (hereinafter, referred to as "DC-iR") was calculated by a voltage drop obtained in a state in which each lithium secondary battery was subjected to a discharge pulse at 2.5 C for 10 seconds, and initial resistance and resistance after 100 cycles were respectively measured.

Thereafter, each of the resistance values measured was substituted into the following [Equation 2] to calculate a resistance increase rate (%), and the results thereof are presented in FIG. 1. In this case, the voltage drop was measured using PNE-0506 charge/discharge equipment (manufacturer: PNE SOLUTION Co., Ltd., 5 V, 6 A).

Resistance increase rate (%)={(resistance after 100 cycles−initial resistance)/(initial resistance)}× 100(%) [Equation 2]

Referring to FIG. 1, with respect to the lithium secondary battery prepared in Example 1, since a chain decomposition reaction of the electrolyte was suppressed even in a case where 100 cycles of charge and discharge were performed at a high temperature (45° C.) in comparison to the lithium secondary batteries prepared in Comparative Examples 1 to 3, a loss of reversible lithium ions was minimized, and thus, it may be confirmed that discharge capacity retention (%) after 100 cycles was improved and resistance increase rate (%) was reduced.

2. Experimental Example 2: High-Temperature (60° C.) Storage Characteristics Evaluation After each of the lithium secondary batteries prepared in Example 1 and Comparative Examples 1 to 3 was activated at a CC of 0.1 C, degassing was performed.

Thereafter, each lithium secondary battery was charged at a CC of 0.33 C to 4.20 V under a constant current-constant voltage (CC-CV) condition at 25° C., then subjected to 0.05 C current cut-off, and discharged at a CC of 0.33 C to 2.5 V. The above charging and discharging were defined as one cycle, and 3 cycles were performed.

Next, each lithium secondary battery was recharged at a CC of 0.33 C to a state of charge (SOC) of 100% and then stored at a high temperature (60° C.) for 4 weeks. In this case, after each of the lithium secondary batteries stored at the high temperature for 0 week, 2 weeks, and 4 weeks was charged to a state of charge (SOC) of 50% at 25° C., DC-iR was calculated by a voltage drop obtained in a state in which each of the lithium secondary batteries was subjected to a discharge pulse at 2.5 C for 10 seconds, the DC-iR was substituted into the following [Equation 3] to calculate a resistance increase rate (%), and the results thereof are presented in FIG. 2. In this case, the voltage drop was measured using PNE-0506 charge/discharge equipment (manufacturer: PNE SOLUTION Co., Ltd., 5 V, 6 A).

Resistance increase rate (%)={(resistance after high-temperature storage−initial resistance)/(initial resistance)}×100(%) [Equation 3]

Figure 2:
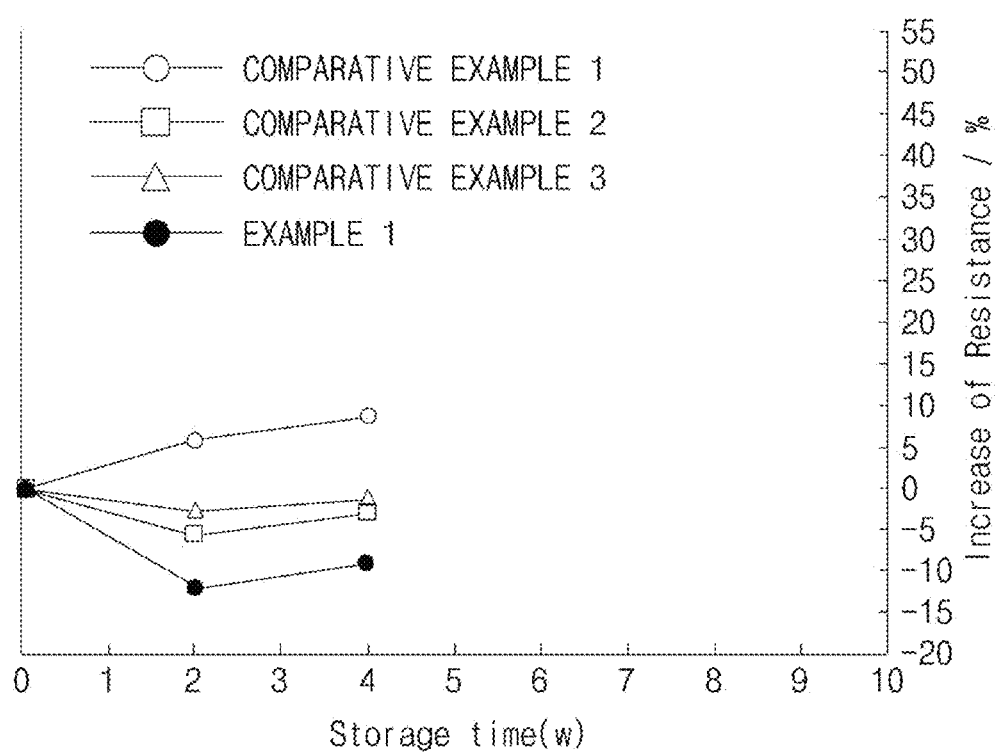
FIG. 2 is a graph illustrating resistance increase rates of lithium secondary batteries measured according to Experimental Example 2.

Referring to FIG. 2, it may be confirmed that the resistance increase rate of the lithium secondary battery prepared in Example 1 was lower than those of the lithium secondary batteries prepared in Comparative Examples 1 to 3 even after high-temperature storage for 4 weeks.

This is considered due to the fact that, with respect to the lithium secondary battery prepared according to the example, since the SEI was stably formed on the surface of the negative electrode and the Lewis acid by-product generated while the lithium salt in the electrolyte was decomposed was also scavenged, the damage of the SEI was suppressed even in a case where the battery was exposed to high temperatures.

The invention claimed is:

1. An electrolyte for a lithium secondary battery, the electrolyte comprising:
 a lithium salt, wherein the lithium salt comprises $LiPF_6$;
 a first additive;
 a second additive; and
 an organic solvent,
  wherein the first additive comprises a compound represented by Formula 1, and
  wherein the second additive comprises a compound represented by Formula 2:

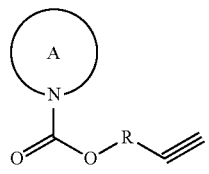

[Formula 1]

wherein, in Formula 1,
 R is a substituted or unsubstituted alkylene group having 1 to 5 carbon atoms, and
 A is a substituted or unsubstituted hetero ring connected by the nitrogen (N) in Formula 1 to the remainder of Formula 1, the substituted or unsubstituted hetero ring having 3 to 8 carbon atoms which contains at least one nitrogen atom and at least one double bond,

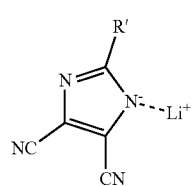

[Formula 2]

wherein, in Formula 2,
 R' is at least one functional group selected from the group consisting of F, $CF_3$, $CHF_2$, $CH_2F$, $C_2HF_4$, $C_2H_2F_3$, $C_2H_3F_2$, $C_2F_5$, $C_3F_7$, $C_3H_2F_5$, $C_3H_4F_3$, $C_4F_9$, $C_4H_2F_7$, $C_4H_4F_5$, $C_5F_{11}$, $C_3F_5OCF_3$, $C_2F_4OCF_3$, $C_2H_2F_2OCF_3$, and $CF_2OCF_3$.

2. The electrolyte for a lithium secondary battery of claim 1, wherein the compound represented by Formula 1 is selected from the group consisting of compounds represented by Formulae 1A to 1C:

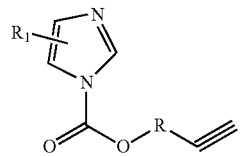

[Formula 1A]

wherein, in Formula 1A,
 R is a substituted or unsubstituted alkylene group having 1 to 5 carbon atoms, and
 $R_1$ is selected from the group consisting of hydrogen, an alkyl group having 1 to 5 carbon atoms, and an alkyl group having 1 to 5 carbon atoms in which at least one hydrogen atom is substituted with a halogen atom,

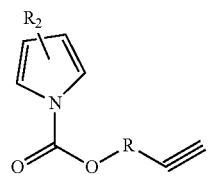

[Formula 1B]

wherein, in Formula 1B,
 R is a substituted or unsubstituted alkylene group having 1 to 5 carbon atoms, and
 $R_2$ is selected from the group consisting of hydrogen, an alkyl group having 1 to 5 carbon atoms, and an alkyl group having 1 to 5 carbon atoms in which at least one hydrogen atom is substituted with a halogen atom,

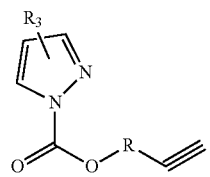

[Formula 1C]

wherein, in Formula 1C,
 R is a substituted or unsubstituted alkylene group having 1 to 5 carbon atoms, and
 $R_3$ is selected from the group consisting of hydrogen, an alkyl group having 1 to 5 carbon atoms, and an alkyl group having 1 to 5 carbon atoms in which at least one hydrogen atom is substituted with a halogen atom.

3. The electrolyte for a lithium secondary battery of claim 1, wherein the compound represented by Formula 1 is selected from the group consisting of compounds represented by Formulae 1A-1 to 1A-5:

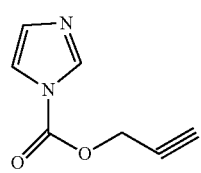

[Formula 1A-1]

-continued

[Formula 1A-2]
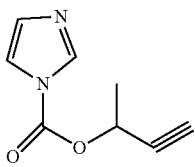

[Formula 1A-3]
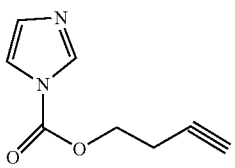

[Formula 1A-4]
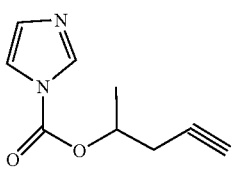

[Formula 1A-5]
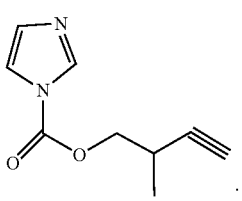

4. The electrolyte for a lithium secondary battery of claim 1, wherein the compound represented by Formula 2 is lithium 4,5-dicyano-2-(trifluoromethyl) imidazole.

5. The electrolyte for a lithium secondary battery of claim 1, wherein the first additive is present in an amount of 0.02 part by weight to 1.0 part by weight, based on 100 parts by weight of the electrolyte.

6. The electrolyte for a lithium secondary battery of claim 1, wherein the first additive is present in an amount of 0.3 part by weight to 1.0 part by weight, based on 100 parts by weight of the electrolyte.

7. The electrolyte for a lithium secondary battery of claim 1, wherein the second additive is present in an amount of 0.02 part by weight to 1.0 part by weight, based on 100 parts by weight of the electrolyte.

8. The electrolyte for a lithium secondary battery of claim 1, wherein the second additive is present in an amount of 0.3 part by weight to 1.0 part by weight, based on 100 parts by weight of the electrolyte.

9. The electrolyte for a lithium secondary battery of claim 1, wherein the lithium salt further comprises $LiBF_4$.

10. A lithium secondary battery, comprising:
a positive electrode;
a negative electrode; and
the electrolyte of claim 1.

* * * * *